United States Patent [19]

Alstetter et al.

[11] Patent Number: 4,801,336
[45] Date of Patent: Jan. 31, 1989

[54] PROCESS FOR ACCELERATING THE TRANSFER OF MEDIA IN A FLUIDIZED BED

[75] Inventors: Franz Alstetter, Karlsfeld; Guenther Hultsch, Oberschleissheim, both of Fed. Rep. of Germany

[73] Assignee: Krauss-Maffei A.G., Fed. Rep. of Germany

[21] Appl. No.: 95,582

[22] Filed: Sep. 9, 1987

Related U.S. Application Data

[62] Division of Ser. No. 685,233, Dec. 21, 1984, Pat. No. 4,710,356.

[30] Foreign Application Priority Data

Dec. 23, 1983 [DE] Fed. Rep. of Germany ....... 3346861

[51] Int. Cl.$^4$ .............................................. C02F 3/08
[52] U.S. Cl. ...................................... 134/32; 134/34; 422/140; 210/617
[58] Field of Search ............... 422/140, 144, 145, 147; 431/7, 170; 432/15, 58; 34/57 A; 134/32, 34, 25.1; 210/617

[56] References Cited

U.S. PATENT DOCUMENTS 3,912,002 10/1975 Elliott ................................. 165/104
4,039,272 8/1977 Elliott ................................. 165/104
4,130,944 12/1978 Hultsch et al. .
4,161,103 7/1979 Horgan et al. .
4,242,450 12/1980 Honda et al. .
4,282,009 8/1981 Belke et al. .
4,343,624 8/1982 Belke et al. .

FOREIGN PATENT DOCUMENTS 2529614 7/1975 Fed. Rep. of Germany .
2545680 10/1975 Fed. Rep. of Germany .
2629958 7/1976 Fed. Rep. of Germany .
1065521 7/1952 France .
54-114474 9/1979 Japan .
54-141379 11/1979 Japan .
615841 1/1976 Switzerland .
1072908 12/1974 United Kingdom .
1581672 5/1977 United Kingdom .

OTHER PUBLICATIONS

"Lexicon der Verfahrenstechnik", Encyclopedia of Process Technology, vol. 16, Fourth Edition, p. 585, by Lueger.

Primary Examiner—Benoit Castel
Attorney, Agent, or Firm—Robert J. Koch

[57] ABSTRACT

A method for accelerating the transfer of media between materials reacting in a fluidized bed in a centrifuge. The rotating fluidized bed increases the relative boundary layer velocities of the phases and assists in the transfer of material across the interface.

6 Claims, 2 Drawing Sheets

A PROCESS FOR ACCELERATING THE TRANSFER OF MEDIA IN A FLUIDIZED BED This application is a division of application Ser. No. 685,233 filed Dec. 21, 1984 now U.S. Pat. No. 4,710,356 the disclosure of which is incorporated herein.

BACKGROUND OF THE INVENTION

The invention relates to a process for reacting two media in a fluidized bed.

It is known from the literature to increase the relative velocity between finely grained solid particles and a liquid carrier flow by means of a fluidized bed arrangement (see Lueger, "Lexicon der Verfahrenstechnik" ("Encyclopedia of Process Technology"), Vol. 16, Fourth Edition, page 585). However, particularly in the case of small particle sizes and small differences in density, the Archimedes numbers are so small that the transfer of material is only negligibly enhanced by a fluidized bed arrangement. In this case, the wetted solid particles remain surrounded by a boundary layer of the liquid and no relative velocity sufficient for a good transfer of material may be achieved within this boundary layer. The mechanism which then overwhelmingly determines the rate of the reaction is diffusion in the boundary layer.

SUMMARY OF THE INVENTION

It is therefore an object of the present invention to accelerate the chemical, biochemical, metallurgical or catalytic reaction between two media, the liquid and solid phases, by increasing the relative velocity at the boundary layers of the phases. Thus, the rates of material transfer particularly in the case of media with small particle size and/or small differences in density are also enhanced.

This object is attained by means of the process according to the present invention. While an increase in the Archimedes number by only a factor of 5 may be obtained with conventional fluidized bed methods, the Archimedes numbers according to the invention may be increased in proportion to the centrifugal acceleration, i.e., a factor of at least 1000 for example. This leads to the advantage that good material exchange rates may be obtained in the field of biotechnology where, for example microbiological cultures grown on solid particles (bacteria, cells, enzymes, etc.) effect the transfer of material as in the treatment of waste waters by means of the so-called fermentation process.

In a preferred embodiment, a fluidized bed is formed subject to a centrifugal field by the cylindrical sieve of a rotatable sieve drum. The drum is provided with means for generating a pressure gradient. A first phase which maintains a second phase in suspension passes through the cylindrical sieve essentially in the radial direction and flows through the second, suspended phase. Uniform flow conditions over the entire surface of the fluidized bed are assured by means of the cylindrical sieve surface and the flow pressure drop it produces. The arrangement of feed and discharge means thus presents no technical difficulties and a continuous operation of the fluidized bed arrangement according to the invention is possible.

In order to accelerate the reaction between to media—a flowing medium with a lower density and a suspended phase with a higher density—it is appropriate to design the sieve drum so that the pressure gradient necessary for the flow may be controlled in a simple manner. According to the invention, this control is achieved by adjusting a first skimming tube and/or filling an annular chamber to a greater height.

The reaction chamber is preferably bounded by a second, radially disposed inner cylindrical sieve. The fluidized bed flow in the reaction chamber may thus be kept free of the flow interference caused by the first skimming tube. The radially disposed inner perforated cylinder may be equipped with filter medium means, so that even the finest particles are retained in the reaction space.

According to another advantageous embodiment, an annular chamber and a feed line are designed as a closed system. This allows an admission pressure to be applied to the flowing medium in addition to the hydrostatic pressure of the radial liquid column. Similarly, a negative pressure may be applied for short periods of time for countercurrent rinsing of the filter medium.

It is possible, according to a further embodiment, to introduce a gaseous reaction medium, such as finely distributed oxygen for example to the execution and acceleration of aerobic processes, such as the biological decomposition of harmful substances in waste waters.

According to a further embodiment, it is possible to add other solid and/or liquid reaction media to the reaction space, continuously or periodically. Thus, additional reaction media may be fed into the reaction space directly through the internal space of the sieve drum or through the feed lines of the solid and/or liquid phases.

According to a particularly advantageous embodiment, all liquid and/or solid media may be processed independent of their densities with only one apparatus.

Preferably, apparatus used in the inventive method is equipped with filter medium means to retain the fine particles entrained by the flowing phase.

Further objects, features and advantages of the present invention will become apparent from the detailed description of preferred embodiments which follows, when considered together with the attached figures of drawing.

DETAILED DESCRIPTION OF THE DRAWINGS

Figure 1:
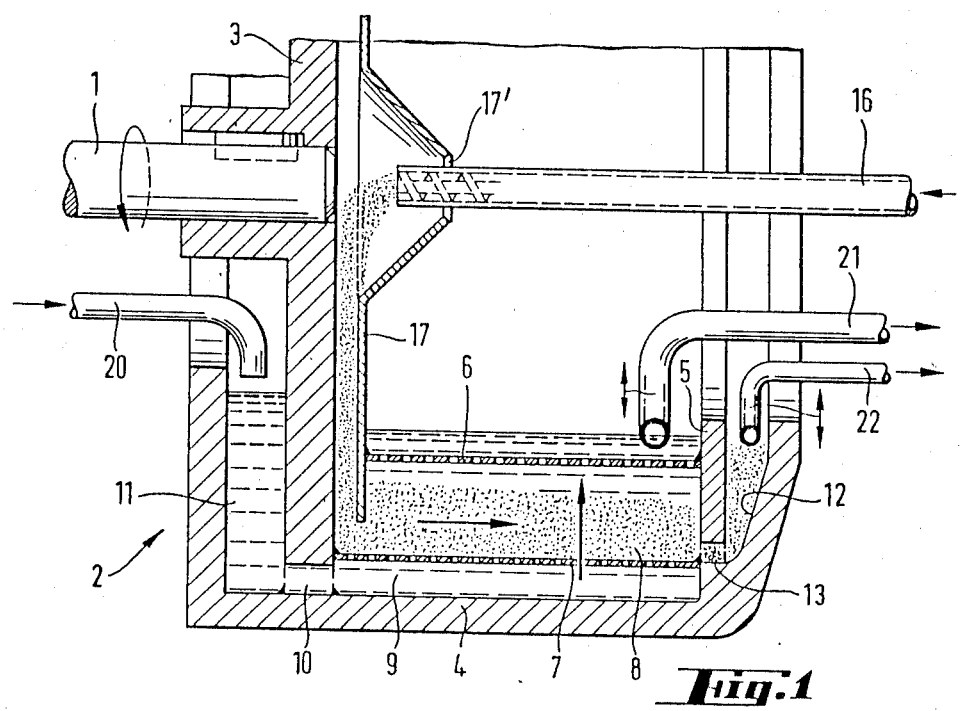
FIG. 1 shows a longitudinal section through a fluidized bed sieve drum.
Figure 3:
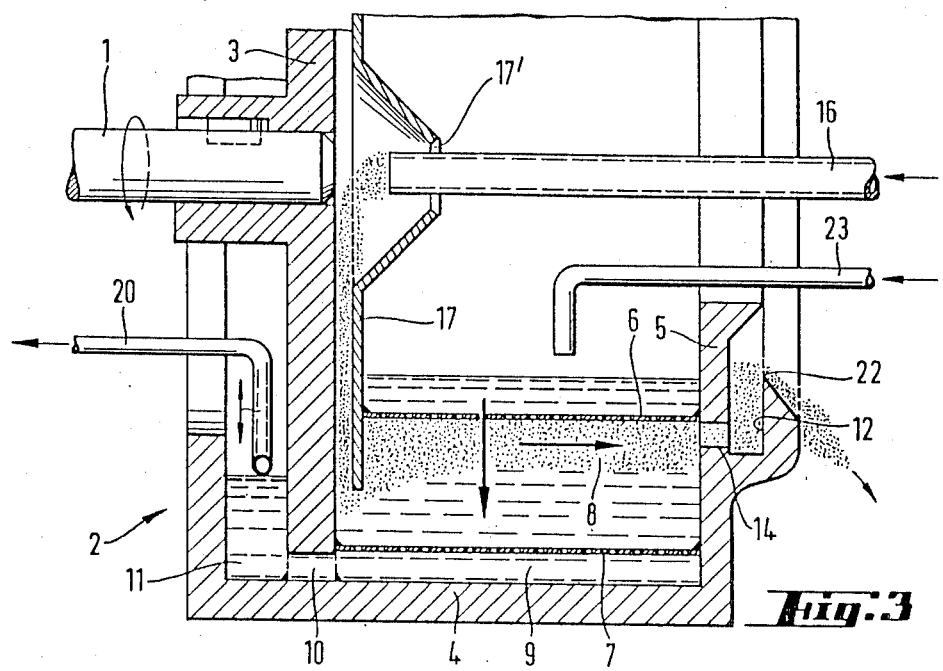
FIG. 3 shows a longitudinal section through a further embodiment of the fluidized bed sieve drum.
Figure 4:
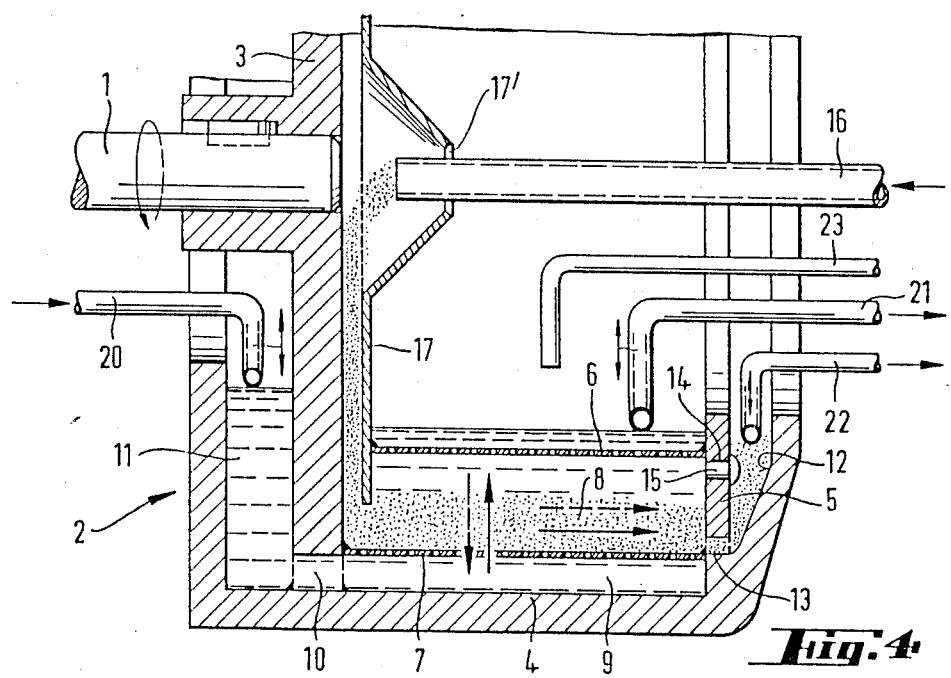
FIG. 4 shows a longitudinal section through a general embodiment of a fluidized bed sieve drum.

According to FIGS. 1, 3 and 4, a sieve drum 2 is fastened to a rotatably supported shaft 1. The sieve drum comprises essentially a drum bottom 3, a drum wall 4 and an annular rim 5. A radially inner and radially outer perforated cylinder 6 and 7 are arranged within the sieve drum 2. The cylinders enclose a reaction space 8. A pressure chamber 9 is connected radially outside of the outer cylindrical sieve 7. The pressure chamber is connected with an annular chamber 11 axially following the drum bottom 3 by means of a circulation bore 10. An annular discharge chamber 12, axially outside an annular rim 5, communicates with the reaction chamber 8 by means of a radially outer discharge bore 13, according to the embodiment in FIG. 1. In the embodiment according to FIG. 3 the discharge chamber is connected with the reaction chamber by means of a radially inner discharge bore 14. The embodiment according to FIG. 4 has both radially inner and the radially outer discharge bores 13 and 14 in the annular rim 5. The discharge bores may be alternately closed by means of a stopper 15. In FIG. 4, the radially inner discharge bore 14 is closed, so that the sieve drum 2 functionally corresponds to the embodiment according to FIG. 1.

According to FIGS. 1-4, a central filling pipe 16, secured against rotation, extends into the internal space of the sieve drum 2. The filling pipe opens into a central orifice 17' of a guide disk 17 mounted parallel to and spaced apart from the drum bottom 3. At its outer edge, the guide disk 17 forms an annular orifice with the drum bottom 3. The orifice leads into the reaction space 8. The central filling pipe 16 may be optionally equipped with a conveyor screw.

Figure 2:
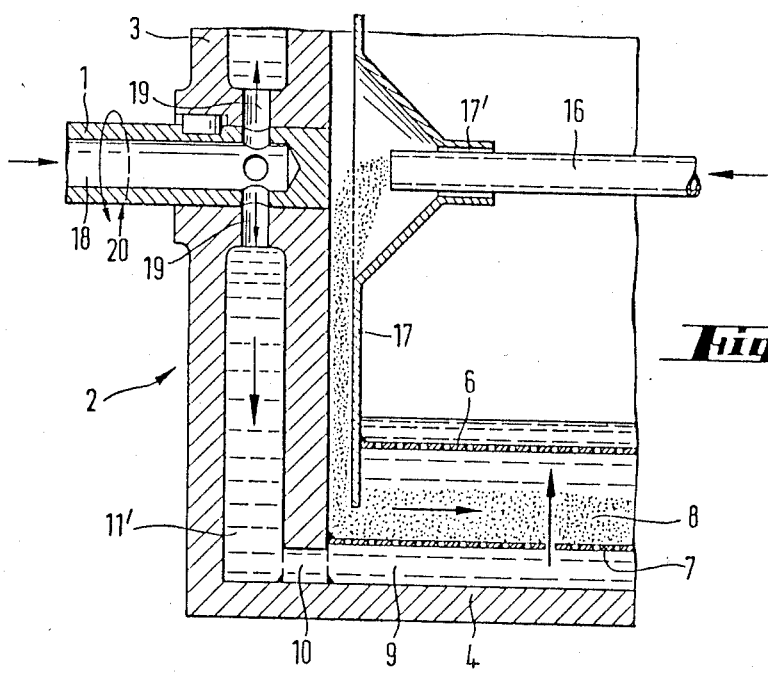
FIG. 2 shows a longitudinal section through a partial area of a fluidized bed sieve drum with an annular chamber.

According to FIG. 2, the shaft 1 is provided with a bore 18, from which radially oriented channels 19 are provided which lead into a closed annular chamber 11'.

According to FIG. 1, a feed line 20 opens into the annular chamber 1. A first skimming tube 21 projects into the inner space of the sieve drum. The skimming orifice of the tube 21 may be adjusted in the radial direction, in steps if necessary. A second skimming tube 22 projects into the annular discharge chamber 12. The second tube can also be arranged in a radially adjustable manner.

The apparatus of FIGS. 1 and 2 are suitable for acclerating a reaction between two media, in which a flow phase has a lesser density and a suspended phase, which is suspended in a centrifugal field in a fluid bed, has a greater density.

The fluid bed is formed in the embodiment according to FIG. 1 by passing the phase with the lower density through the line 20 and into the annular chamber 11. A liquid column of a given radial height is thus established in the chamber 11. The phase with the lower density flows through the circulating bore 10 and into the pressure chamber 9. From there, the phase with the lower density flows radially inwardly through the radially outer cylindrical sieve 7, so as to impact the phase with the higher density and maintain the latter in suspension. The higher density phase passes through the central filling pipe 16, through the intermediate space formed by the drum bottom 3 and the guide disk 17, into the reactor chamber, and is distributed in a suspended flow over the radially outer sieve surface 7. The lower density phase, which flows radially inward through the higher density phase, is removed following reaction in the reaction chamber 8 by the first skimming tube 21 at the radial height of the annular rim 5 and discharged to the outside. The higher density suspended phase travels in the axial direction to the radially outer discharge bore 13, and passes into the annular discharge chamber 12, from whence it is removed by the second skimming tube 22. In order to prevent interference with the fluid bed flow established in the reaction chamber 8 by the immersion of the first stripper tube 21, the radially inner cylindrical sieve 6 serves as a shielding device. A filter medium (not shown) may be arranged on the inner perforated cylinder in order to retain the fine particles entrained by the fluid bed flow.

The suspended state of the solid phase of higher density is obtained by a particular hydrostatic pressure gradient which is established between the annular chamber 11 and the reaction chamber 8. The pressure gradient is formed as a function of the density values of the two media and the rotating velocity of the sieve drum 2. This pressure gradient may be determined by the feed volume and by the radial height setting of the first skimming tube 21.

The pressure gradient creating the suspension may be obtained according to the embodiment of FIG. 2 by designing the annular chamber 11 as a closed system into which the phase of lower density may be introduced under pressure through a bore feed 18 and radially oriented channels 19. A higher hydrostatic pressure may be established in the annular chamber 11, which extends to the shaft 1, by means of a higher radial fluid column.

The exemplary apparatus depicted in FIG. 3 is suitable for accelerating a reaction between two media, in which the flowing phase has a higher density and the phase suspended in a centrifugal field has a lower density.

The fluid bed is formed according to the embodiment of FIG. 3 as follows. The higher density phase is introduced into the inner space of the sieve drum 2 by means of a filling pipe 23. A radially outward directed flow enters through the radially inner cylindrical sieve 6 to impact the solid phase of lower density. The flow passes through the solid phase in a manner such that the latter is maintained in suspension over the radially inner cylindrical sieve 6. The lower density phase passes through the central filling pipe, through the space formed by the drum bottom 3 and the guide disk 17, and into the reaction chamber 8. From there lower density phase is distributed in a floating flow motion over the radially inner cylindrical sieve 6. The higher density phase, which flows through the lower density phase in the radially outward direction, reaches the pressure chamber defined by the drum wall 4, from whence it flows through the circulation bore 10 and into the annular chamber 11. The fill height in the annular chamber 11 is determined by the line 20, which acts as a skimming tube and removes the higher density phase at a particular radial height. A hydrostatic pressure gradient is thus established between the reaction chamber 8 and the annular chamber 11. The pressure gradient effects the outwardly directed flow of the higher density phase.

The discharge of the lower density phase, which is conveyed by the fluid bed through the radially inner discharge bore 14 into the annular discharge chamber 12, may be carried out by a radially and, if need be, intermittently adjustable second skimming tube 22 (FIG. 1). As shown in FIG. 3, the lower density phase may also be discharged over a discharge edge 22'; as the lower density phase rises to the surface in the annular discharge chamber 12, it is automatically conveyed over the discharge edge.

The radially outward directed flow of the higher density phase may be achieved or promoted according to the embodiment of FIG. 2, in that the centrifuge space is designed as a closed system and exposed to an overpressure. The liquid phase is thereby conveyed into the space outside the centrifuge under normal pressure.

To retain the fine particles entrained by the fluid bed flow, a radially outer perforated cylinder 7 may be provided, which may optionally be covered by filter medium means.

The embodiment according to FIG. 4, represents a combination of the embodiments according to FIGS. 1 and 3. In this embodiment, the feed line 20, which extends into the annular chamber 11, may also be used as a stripper tube with a radially adjustable skimming orifice. Both a filling pipe, corresponding to the embodiment of FIG. 3, and a first skimming tube 21, corresponding to the embodiment of FIG. 1, extend into the internal space of the sieve drum 2. When the radially outer discharge bore 13 is open, the fluid bed sieve drum is operable as in the embodiment of FIG. 1. The line 20 may serve as the feeder line for the lower density phase while the feeder pipe 23 remains idle. The first skimming tube 21 may serve as the outlet for the lower density phase after its flow through the reaction chamber 8. The flow direction of the two media of different density which flow through each other is indicated by the arrows with solid lines.

If the radially outer discharge bore 13 is closed instead of the radially inner discharge bore 14, the fluid bed sieve drum is operated as in the embodiment of FIG. 3. In this case, line 20 is used as a skimming tube and filler pipe 23 is employed in place of the first skimming tube 21. The flow direction of the two converging media of different densities is represented by arrows with broken lines.

As in the apparatus of FIGS. 1 and 3, the apparatus according to FIG. 4 may also be equipped with a closed annular chamber according to FIG. 2, in which the medium may be fed under pressure or from which it may be removed, through the bore 18 and the channels 19, by means of a reduced pressure.

Further reactants may be introduced into the reaction chamber in the gaseous, liquid or solid state through the feed lines of all of the embodiments—such as the central filling line 16, the bore 18 with the channels 19, the line 20 serving as the feeder line and the filler pipe 23. Thus, for example, for the execution and acceleration of aerobic processes, such as the biological decomposition of harmful substances in waste waters, finely distributed air may be introduced through the bore 18 and conveyed through the radially outer sieve surface 7 to the reaction chamber 8. Similarly, catalytically active solids may be introduced into the reaction chamber through the central filling pipe 16 and the guide disk 17. In principle, all types of additional reactants may be fed into the central inner space of the fluid bed sieve drum or the annular chamber 11 through separate lines.

As a rule, the suspended phase will consist of finely grained solid particles, kept in suspension by the flowing phase, the reaction liquid of the fluidized bed or vortex layer.

In principle, a medium which has a higher density than another medium may have a lower specific weight by virtue of gas formation or gas bonding allowing it to float. In this case, the embodiment of FIG. 3 is preferred, in which the phase tending to float is treated as a phase of lower density.

What is claimed is:

1. A method for contacting a flowing liquid of lower density with a medium of higher density comprising solid particles, said method comprising:
   introducing said liquid of lower density into a radially outer zone within a centrifuge,
   introducing said medium of higher density into a radially inner zone within said centrifuge wherein said inner zone and said outer zone are separated by a perforated surface,
   rotating said radially inner zone to force said medium of higher density radially outward toward said radially outer zone;
   flowing said liquid of lower density radially inward toward said radially inner zone and in contact with said medium of higher density to form a reaction bed, and
   independently withdrawing said liquid and said medium of higher density.

2. A method as in claim 1, further comprising controlling the rate of inward radial flow of said liquid by controlling the rate of withdrawal of said liquid after said liquid has contacted said medium of higher density.

3. A method as in claim 2, wherein said radially outer zone communicates with an annular chamber having liquid at a radial height.

4. A method as in claim 3, wherein said control is achieved by controlling said radial height of said liquid.

5. A method as in claim 3, wherein said annular chamber forms a closed system with a feed line for said liquid and said control is achieved by controlling the admission pressure of said liquid.

6. A method of contacting a medium of lower density comprising solid particles with a liquid of higher density, said method comprising:
   introducing said medium of lower density into a radially outer zone with a centrifuge,
   introducing said liquid of higher density into a radially inner zone within said centrifuge wherein said inner zone and said outer zone are separated by a perforated surface,
   rotating said inner zone to force said liquid radially outward to said outer zone and in contact with said medium of lower density to form a reaction bed, and
   independently withdrawing said liquid and said medium of lower density.

* * * * *